United States Patent
Yue et al.

(10) Patent No.: US 10,058,691 B2
(45) Date of Patent: Aug. 28, 2018

(54) DISPOSABLE ARRAY-TYPE MICRO INJECTION NEEDLE HEAD AND PREFILLED SYRINGE

(75) Inventors: Ruifeng Yue, Beijing (CN); Yan Wang, Beijing (CN)

(73) Assignee: TSINGHUA UNIVERSITY, Beijing (CN)

(*) Notice: Subject to any disclaimer, the term of this patent is extended or adjusted under 35 U.S.C. 154(b) by 826 days.

(21) Appl. No.: 14/352,987

(22) PCT Filed: Aug. 7, 2012

(86) PCT No.: PCT/CN2012/079773
§ 371 (c)(1),
(2), (4) Date: Apr. 18, 2014

(87) PCT Pub. No.: WO2013/056588
PCT Pub. Date: Apr. 25, 2013

(65) Prior Publication Data
US 2014/0257190 A1   Sep. 11, 2014

(30) Foreign Application Priority Data
Oct. 18, 2011   (CN) .......................... 2011 1 0317397

(51) Int. Cl.
*A61M 5/00*     (2006.01)
*A61M 37/00*    (2006.01)
(Continued)

(52) U.S. Cl.
CPC ........ *A61M 37/0015* (2013.01); *A61M 5/283* (2013.01); *A61M 5/3298* (2013.01);
(Continued)

(58) Field of Classification Search
CPC ... F04C 2270/0421; A61M 2037/0023; A61M 2037/003; A61M 37/0015; A61M 5/3298;
(Continued)

(56) References Cited

U.S. PATENT DOCUMENTS

| 6,146,361 A | * | 11/2000 | DiBiasi | A61M 5/42 604/232 |
| 2003/0050602 A1 | * | 3/2003 | Pettis | A61M 5/28 604/117 |

(Continued)

FOREIGN PATENT DOCUMENTS

| CN | 100998901 A | 7/2007 |
| CN | 102327656 A | 1/2012 |

(Continued)

*Primary Examiner* — Kevin C Sirmons
*Assistant Examiner* — Tiffany Legette-Thompson
(74) *Attorney, Agent, or Firm* — Lathrop Gage LLP

(57) ABSTRACT

The invention discloses a disposable array-type micro injection needle head which comprises a lower needle seat which is configured as a cylindrical column opening at one end and having a top cap at the other end and which is configured to be connected with an injection reservoir; an upper needle seat which is located above the top cap of the lower needle seat with a cavity formed between the upper needle seat and the top cap; a through-hole formed in the top cap which is configured for communicating the cylindrical column with the cavity, wherein a pipetting needle is mounted in the through-hole which has one end communicated with the cavity and the other end located in the cylindrical column and which is configured for extracting injection from the injection reservoir into the cavity; and at least two needle tubes mounted in the upper needle seat, each of which has one end comprising a needle tip for puncturing and for injecting the injection and the other end for mounting on the upper needle seat and for communicating with the cavity. The needle head can be used directly on existing insulin pen, or the cylindrical column can be provided inside it with an injection reservoir to form a disposable prefilled syringe. By using a plurality of thin, short needle tubes for injecting simultaneously, vertical hypodermic injection of medicines such as insulin can be preformed rapidly, leakproof, pain- (Continued)

lessly, safely and conveniently at various sites of a human body, without needing to pinch skin, while a potential trouble that the medicines be injected into muscles can be avoided. Patient adherence to the treatment regimen and the treatment effect are improved.

14 Claims, 7 Drawing Sheets

(51) Int. Cl.
*A61M 5/28* (2006.01)
*A61M 5/32* (2006.01)

(52) U.S. Cl.
CPC ............... *A61M 2037/003* (2013.01); *A61M 2037/0023* (2013.01); *A61M 2037/0061* (2013.01); *F04C 2270/0421* (2013.01)

(58) Field of Classification Search
CPC .......... A61M 5/283; A61M 2037/0061; A61M 37/00
USPC .................................. 604/21, 173, 181, 272
See application file for complete search history.

(56) References Cited

U.S. PATENT DOCUMENTS

| | | | |
|---|---|---|---|
| 2008/0108951 A1* | 5/2008 | Jerde ..................... | A61M 5/002 604/198 |
| 2008/0125745 A1* | 5/2008 | Basu ..................... | A61M 25/00 604/506 |
| 2009/0069753 A1* | 3/2009 | Ruan .................. | A61M 5/3202 604/192 |
| 2009/0247953 A1* | 10/2009 | Yeshurun .......... | A61M 37/0015 604/173 |
| 2011/0092883 A1 | 4/2011 | Uchiyama | |

FOREIGN PATENT DOCUMENTS

| CN | 202342607 U | 7/2012 |
|---|---|---|
| EP | 1852142 A1 | 11/2007 |

* cited by examiner

DISPOSABLE ARRAY-TYPE MICRO INJECTION NEEDLE HEAD AND PREFILLED SYRINGE

TECHNICAL FIELD

The invention relates to medical and beauty equipment and medical technology fields, in particular to a disposable array-type micro injection needle head and a prefilled syringe based on the disposable array-type micro injection needle head.

BACKGROUND ART

Injection technique and injection devices play important roles in the treatment of diabetes, and they are even of equal importance with the choice of an insulin preparation and affect success or failure of glycemic control. Many health care workers and diabetic patients on insulin therapy often ignore the influence of the injection technique itself on the effect of the glycemic control. Clinicians often investigate the reasons why the desired glucose control target is not achieved from the insulin preparation and blood glucose self monitoring point of view, while neglecting the influence of the injection technique itself on the effect of the glycemic control. The process of insulin being injected into a human body by means of the injection device and functioning is of great importance. Insulin absorption rate differs for insulin subcutaneous injection or for insulin intramuscular injection, because absorption rates of insulin differ a lot at different injection locations, and insulin absorptions differ a lot in a stationary state and in a moving state. Optimizing insulin injection technique includes choosing a needle head with an appropriate length, using correct injection technique, regularly changing injection sites, and avoiding intramuscular injection, etc. All these are of great importance for the glucose control.

A research on insulin injection technique situation in China reveals that, for about 31.1% of patients, injection results in a bump at a corresponding injection site, of which 90% are at abdomen. However, there is still part of patients receiving injection at fat tissue hyperplasia sites. Performing injection at the same site repeatingly will cause subcutaneous fat tissue hyperplasia at this site and then a sclerosis generates. Insulin absorption reduces if insulin is injected once again at this site, and absorption of insulin lasts too long results in an unstable glycemic control. The research also reveals that, for about 30% of patients, the skin is not pinched during the injection being performed at abdomen. If it is a needle head of 8 mm that is used in this case, a potential risk of intramuscular injection may be caused, which will accelerate the insulin absorption and adversely affect the effect. Meanwhile, for half of the patients, although the injection is performed with the skin pinched, but the skinfolds are released prematurely. In fact, other than abdomen, other sites of a human body such as lateral thigh, lateral ¼ location of arm and buttock are also suitable for insulin injection. Regularly changing injection sites means regularly changing injection sites among abdomen, arm, thigh and buttocks. Treatment effect can be improved and complication probability can be reduced by regularly changing injection sites. Injection angles and injection methods vary due to different lengths of insulin injection needle heads. Injections should be performed with a 45 degrees angle and with the skin pinched if the needle head adopted has a length of 8 mm or 12.7 mm, in order to increase the thickness of subcutaneous tissue and to reduce the risk that insulin being injected into an intramuscular layer. Injections can be performed vertically without needing to pinch the skin if an ultra-thin and ultra-short needle head of 5 mm length is adopted, as long as the entire needle head pierces into the subcutaneous tissue. Pain can be alleviated and injection adherence can be improved with the needle head of 5 mm.

Insulin pen injection is widely used on patients with diabetes due to its properties of easy to learn, accurate dose, convenient and durable, slight pain, good effect, etc. In clinical Applications, injection is performed by means of a novo pen and a HumaPen Ergo II in cooperation with a needle head of 8 mm×30 G. According to operating instructions, the needle head should stay in the skin more than 6 s to 10 s after injection while a push button is pressed down, until the needle head is pulled out. During practice, due to medicine liquid injected subcutaneously can not be diffused and absorbed fully in a short time, a little medicine liquid drops off the needle head even if the operation is performed according to the operating instructions. Thus, the accuracy of treatment dose can not be guaranteed.

A needle tube of an existing disposable injection needle head generally has a length more than 15 mm, and even an ultra-fine needle tube of 0.25 mm diameter deployed in a disposable injection needle head for an insulin pen has a length up to 4.5 mm to 12 mm. In this case, vertical injection can not be directly performed at locations, for example at arm, if the skin is not pinched, and patients especially children are terrified by the pain caused by the injection. Due to only one needle tube for one needle head, for the same dose to be injected, although a shorter needle tube may cause alleviated pain, the needle head has to stay in the skin during the injection and after the injection, and the time it will take for the medicine liquid to be sufficiently absorbed during which the patients have to wait will consequentially increase. These factors will undoubtedly bring much inconvenience to the patients. As a result, it is easier said than done, and the patient adherence to proper treatment regimen is reduced and thus the effect is adversely affected.

In addition, a disposable injection needle head on the existing insulin pen has to be used in combination with the insulin pen, and the disposable injection needle head and the insulin pen are stored separately from each other when not in use and assembled temporarily when in use. As a result, the whole injection device is bulky and heavy and thus is only applied to insulin injection.

SUMMARY OF THE INVENTION

Technical Problems to be Solved

A technical problem to be solved is how to perform vertical hypodermic injection of medicine, such as insulin or the like, rapidly, leakproof, painlessly, safely, and conveniently at target sites such as abdomen, arms, thighs, buttock etc, while capable of effectively avoiding muscle injection, in order to improve patient adherence to the treatment regimen and stability of effect, to alleviate pain and to reduce complication probability. Another technical problem to be solved is how to enable to inject varieties medicines with a needle head and to improve the convenience of application of a syringe.

Technical Solutions

For solving a first one of the above technical problems, the invention provides a disposable array-type micro injection needle head which comprises:

a lower needle seat which is configured as a cylindrical column opening at one end and having a top cap at the other end and which is configured to be connected with an injection reservoir;

an upper needle seat which is located above the top cap of the lower needle seat with a cavity formed between the upper needle seat and the top cap;

a through-hole formed in the top cap which is configured for communicating the cylindrical column with the cavity, wherein a pipetting needle is mounted in the through-hole which has one end communicated with the cavity and the other end located in the cylindrical column and which is configured for extracting injection from the injection reservoir into the cavity; and at least two needle tubes mounted in the upper needle seat, each of which has one end comprising a needle tip for puncturing and for injecting the injection and the other end for mounting on the upper needle seat and for communicating with the cavity.

In the disposable array-type micro injection needle head, the top cap is provided above it with a positioning wall which is integrally formed with the lower needle seat and which is configured for fixing and sealing the upper and lower needle seats.

In the disposable array-type micro injection needle head, the upper needle seat is fixed and sealed to the positioning wall by means of structural adhesive or rubber pads or combination thereof.

In the disposable array-type micro injection needle head, the top cap is provided under it with a fixing groove which is coaxial and communicated with the through-hole, wherein the fixing groove has an inner diameter equal to or larger than an inner diameter of the through-hole or an outer diameter of the pipetting needle, and the pipetting needle extending through the fixing groove is sealingly fixed in the fixing groove and in the through-hole by means of the structure of the fixing groove itself or structural adhesive.

In the disposable array-type micro injection needle head, the top cap is provided under it with a fixing groove which is coaxial and communicated with the through-hole, wherein the fixing groove has an inner diameter smaller than an inner diameter of the through-hole or an outer diameter of the pipetting needle, and the pipetting needle extending through the fixing groove is sealingly fixed in the fixing groove and in the through-hole by means of the structure of the fixing groove itself.

In the disposable array-type micro injection needle head, the lower needle seat is provided on an inner wall or outer wall of the cylindrical column with screw threads and/or fixing snap-slots, so that the lower needle seat is detachably connected with the injection reservoir.

In the disposable array-type micro injection needle head, the needle tube has an outer diameter of 80 μm to 400 μm and an inner diameter of 30 μm to 200 μm, and there is a height of 0.2 mm to 5 mm from a top end of the upper needle seat to the needle tip, and in that the pipetting needle has an outer diameter of 120 μm to 1000 μm and an inner diameter of 50 μm to 500 μm, and there is a length of 0.2 mm to 15 mm from a bottom end of the fixing groove to the needle tip.

In the disposable array-type micro injection needle head, the needle tip is provided at one end or at two opposite ends of the needle tube and of the pipetting needle, wherein the needle tip comprises an elliptical torus or has at least a segment of an arc surface cut from the elliptical torus to form a sharp angle, the elliptical torus forming an angle of 5 degrees to 88 degrees with regard to an axial direction of the needle tube.

In the disposable array-type micro injection needle head, the upper needle seat is a flat substrate or a curved substrate.

In the disposable array-type micro injection needle head, the needle tube and the pipetting needle are made of a metal material, and the upper and lower needle seats are made from one polymer material or more polymer materials, the polymer including plastic, resin and rubber.

In the disposable array-type micro injection needle head, the upper needle seat and/or the lower needle seat is made from one polymer material, and tight fit is established by direct contact between the needle tube and the upper needle seat and/or between the pipetting needle and the lower needle seat.

In the disposable array-type micro injection needle head, the upper needle seat is provided with positioning notches or outlets which have a corresponding number with the needle tubes, and the needle tubes are fixed in corresponding positioning notches or outlets by means of the structure of the positioning notches or outlets themselves or with structural adhesive.

In the disposable array-type micro injection needle head, the positioning notches or outlets are integrally or separately formed with the upper needle seat.

In the disposable array-type micro injection needle head, the upper needle seat is provided with at least one opening or recess in its side wall, and structural adhesive is filled in the opening or recess and surrounds the needle tubes to fix them in the positioning notches or outlets of the upper needle seat.

The disposable array-type micro injection needle head further comprises a needle tube protecting sleeve provided over the upper needle seat, a needle seat protecting sleeve provided over the upper and lower needle seats, and a sealing material layer provided at an opening at a lower portion of the needle seat protecting sleeve, wherein the sealing material layer is preferably a sealing paper.

For solving a second one of the above technical problems, the invention provides a disposable prefilled syringe incorporating a disposable array-type micro injection needle head described above, wherein the disposable prefilled syringe comprises the disposable array-type micro injection needle head and an injection reservoir, wherein the injection reservoir is an enclosed container prefilled with medicine liquid and is located or partially located in the cylindrical column of the lower needle seat, wherein the container has a top end able to be punctured by the pipetting needle and a bottom end at which a movable component or piston is provided, and wherein, in use, the container is manually rotated and/or pressed so that the pipetting needle punctures into the top end of the container and the movable component or piston at the bottom end of the enclosed container presses injection through the pipetting needle to be injected out.

In the disposable prefilled syringe, the disposable array-type micro injection needle head and the injection reservoir are assembled into one piece, and the assembly is sterilized and enclosed within the needle seat protecting sleeve, or in that, the disposable array-type micro injection needle head and the injection reservoir are stored separately from each other when not in use and are assembled into one piece when desired Technical Effect The disposable array-type micro injection needle head constructed as above can be used directly on an insulin pen. By providing the disposable array-type micro injection needle head with a plurality of thin, short and solid needle tubes which are spaced apart from each other by a certain distance and which performs injecting simultaneously, vertical hypodermic injection of medicines such as insulin can be preformed rapidly, leakproof, painlessly, safely and conveniently at sites such as abdomens, arms, thighs, buttock etc, without needing to pinch skin, while a potential trouble that the medicines be injected directly into muscles can be totally avoided. Therefore, an injection tool is provided for patients from the headstream which is capable of regularly changing injection locations, avoiding muscle injection and performing injection painlessly and rapidly, which improves substantially patient adherence to the treatment regimen and stability of effect and has profound significance in glycemic control in patients with diabetes and Rehabilitation. The disposable prefilled syringe provided as above enables the application of the disposable array-type micro injection needle head with regard to medicine category to be widened, has a compact structure, and is easy to use.

LIST OF REFERENCE NUMERALS

1: needle tube; 2: upper needle seat; 3: lower needle seat; 4: pipetting needle; 5: needle tip; 5a: elliptical torus; 5b: sharp angle; 6: structural adhesive; 7: positioning wall; 8: screw threads; 8-1: fixing snap-slot; 9: needle tube protecting sleeve; 10: needle seat protecting sleeve; 11: sealing paper; 12: positioning grove or outlet; 13: recess; 14: opening; 15: cavity; 16: fixing groove; 17: injection reservoir; 18: medicine liquid; 19: material or structure easy to be punctured by pipetting needle; 20: piston; 21: threads connection area between lower needle seat and injection reservoir; 22: top cap; 23: through-hole.

DETAILED DESCRIPTION OF PREFERRED EMBODIMENTS

Special implementations of the invention will be described further in detail in combination with drawings and embodiments. The embodiments herein are merely intended to illustrate the invention, instead of limiting the scope of the invention.

Example 1

Figure 1:
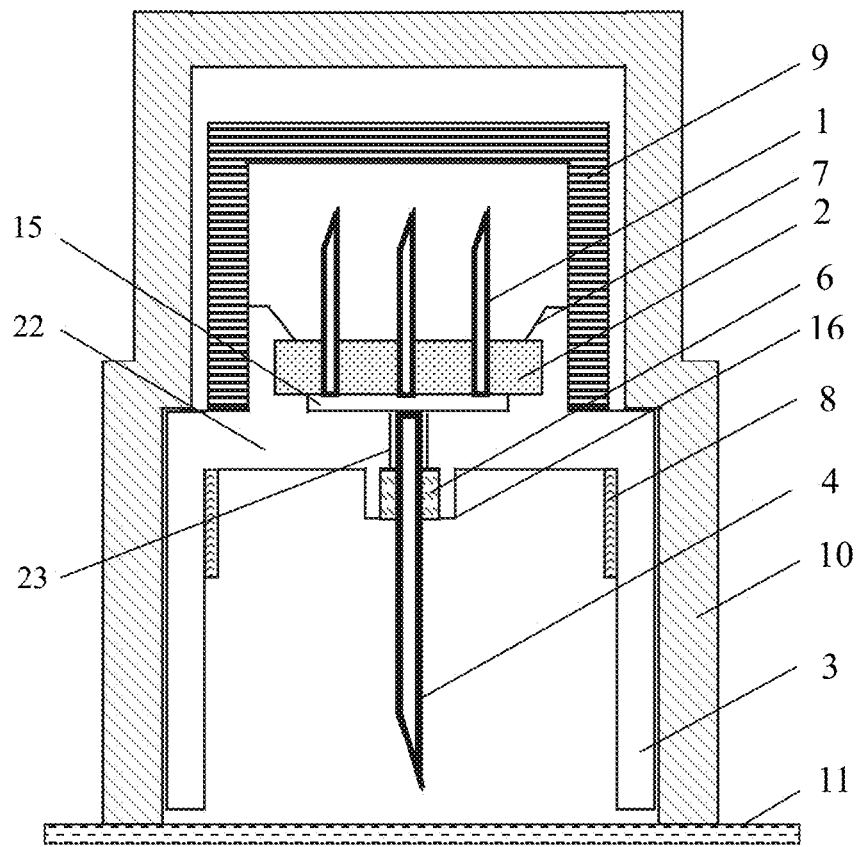
FIG. 1 is a cross sectional view of a structure of a disposable array-type micro injection needle head according to a first embodiment of the invention, in which an upper lower needle seat is a flat substrate.

FIG. 1 is a cross sectional view of a structure of a disposable array-type micro injection needle head according to an embodiment of the invention, in which the disposable array-type micro injection needle head comprises a lower needle seat 3 configured as a cylindrical column opening at one end and comprising a top cap 22 at the other end, the lower needle seat 3 being configured for connecting with an injection reservoir, and an upper needle seat 2 located over the top cap 22 of the lower needle seat 3 with a cavity 15 formed between the upper needle seat 2 and the top cap 22. The top cap is provide with a through-hole 23 for communicating the cylindrical column with the cavity 15, and a pipetting needle 4 is positioned in the through-hole 23. The pipetting needle 4 is a needle tube made of a metal material, has one end communicated with the cavity 15 and the other end located within the cylindrical column, and is configured for extracting injection from the injection reservoir into the cavity 15.

At least two needle tubes 1 are mounted in the needle seat 2, each of which is a short and thin miniature metal needle tube, and the needle tubes 1 are regularly arranged in the needle seat 2 to form a needle tube array. The needle tube 1 has one end comprising a needle tip for puncturing and for injecting the injection and the other end for mounting in the needle seat 2 and for communicating with the cavity 15. The micro injection needle head constructed as above, upon connected with the injection reservoir, extracts injection out of the injection reservoir with its pipetting needle 4, supplies the injection into the cavity 15 between the upper and lower needle seats 2 and 3, and injects the injection out via the needle tube array composed of the needle tubes 1, wherein the cavity 15 plays the role of a manifold for injection from one outlet to several inlets.

Figure 11:
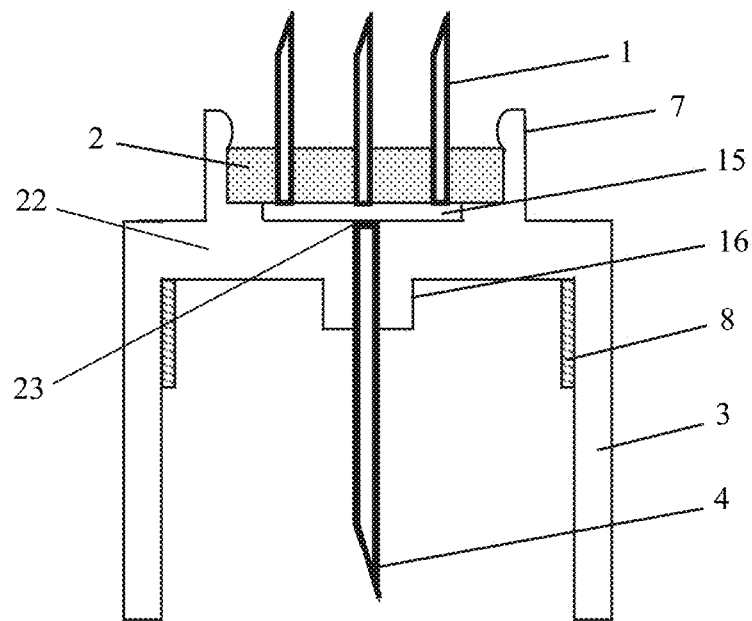
FIG. 11 is a cross sectional view of a structure of a disposable array-type micro injection needle head according to the first embodiment of the invention, in which fixing and sealing can be achieved between needle tubes and an upper needle seat and between a pipetting needle and a lower needle seat by themselves.
Figure 12:
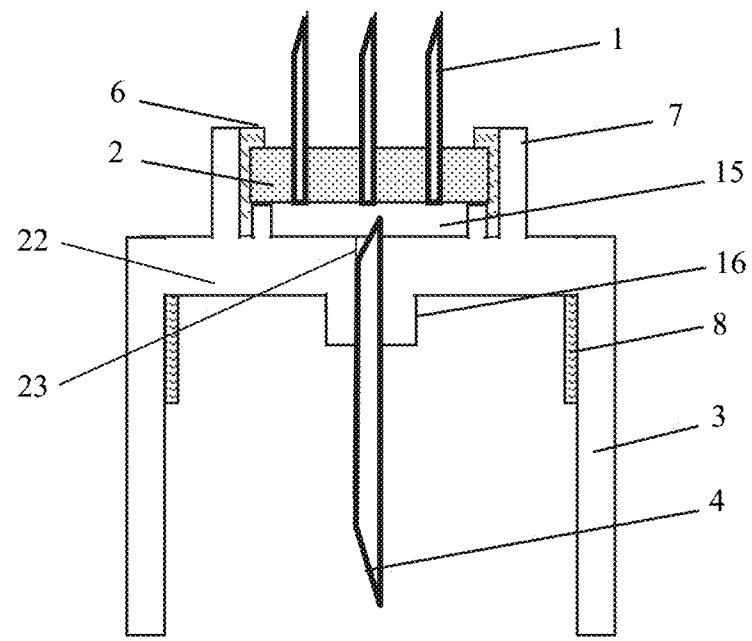
FIG. 12 is a cross sectional view of a structure of a disposable array-type micro injection needle head according to the first embodiment of the invention, in which only fixing and sealing between upper and lower needle seats are achieved by structural adhesive.
Figure 13:
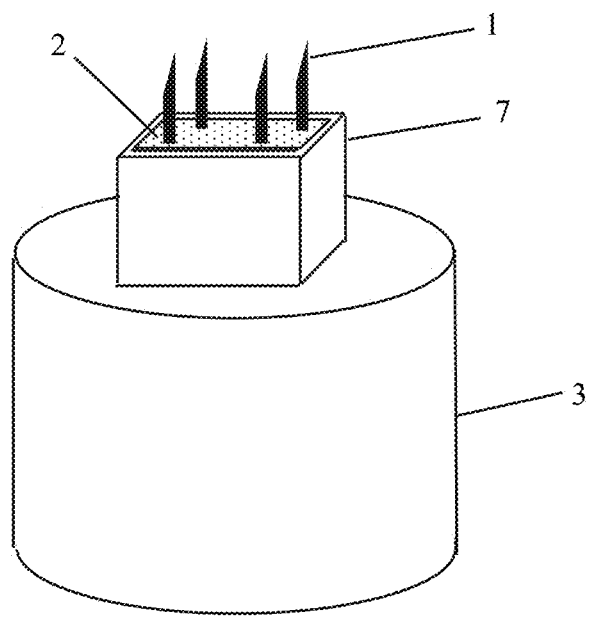
FIG. 13 is a cross sectional view of a structure of a disposable array-type micro injection needle head according to the first embodiment of the invention, in which an upper needle seat is a square flat substrate.

In particular, the lower needle seat 3 is provided above its top cap 22 with a positioning wall 7 for fixing and sealing the upper and lower needle seats, the positioning wall 7 being integrally formed with the lower needle seat. Sealing and fixing between the upper and lower needle seats are achieved by tight contact established between the positioning wall 7 and the upper needle seat, as shown in FIGS. 1 and 11. As a preferred solution, the upper needle seat 2 can be fixed and sealed to the positioning wall 7 with structural adhesive or rubber pads or combination thereof, as shown in FIGS. 11 and 12. The positioning wall 7 has a cross-sectional shape and size corresponding to that of the upper needle seat 2 to ensure that the cavity 15 below the upper needle seat 2 is sealed, as shown in FIG. 13. The lower needle seat 3 is provided with a fixing groove 16 under the top cover which is coaxial and communicated with the through-hole 23 in the lower needle seat 3. The fixing groove 16 has an inner diameter equal to or larger than the inner diameter of the through-hole 23 or an outer diameter of the pipetting needle 4, and the pipetting needle 4 extending through the fixing groove is sealingly fixed in the fixing groove and in the through-hole 23 by means of the structure features of the fixing groove itself or with structural adhesive 6. Or, the inner diameter of the fixing groove 16 is smaller than the inner diameter of the through-hole 23 or the outer diameter of the pipetting needle 4, and the pipetting needle 4 extending through the fixing groove deforms the fixing groove and is sealingly fixed in the fixing groove and in the through-hole 23 by means of the structure features of the fixing groove itself.

The lower needle seat 3 is provided on an inner wall or outer wall of the cylindrical column with screw threads 8, so that the lower needle seat 3 can be detachably connected with the injection reservoir to facilitate replacement of the disposable injection needle head. The screw threads 8 in this embodiment can also be replaced with fixing snap-slots, and correspondingly projections are provided on an outer wall of the injection reservoir. The fixing snap-slots of the lower needle seat 3 can be snapped and fixed on the projections of the injection reservoir by rotating in order to connect the disposable injection needle head with the injection reservoir, and by rotating reversely the disposable injection needle head can be removed. Alternatively, both the screw threads and the fixing snap-slots are provided on the wall of the cylindrical column of the lower needle seat 3 for better mating and cooperating with certain injection reservoirs.

In the injection needle head of the embodiment, a needle tube protecting sleeve 9 is provided over the upper needle seat 2, a needle seat protecting sleeve 10 is provided over the upper and lower needle seats, and a sealing dialysis paper 11 is provided at an opening at a lower portion of the seat protecting sleeve 10. In this way, injection needle head is guaranteed to be aseptic and clean and is protected from being damaged easily. sealing dialysis paper 11, the needle seat protecting sleeve 10 and the needle tube protecting sleeve 9 can be removed in sequence and then the injection needle head is ready to use. In the present embodiment, the upper needle seat 2 is a flat substrate, as shown in FIGS. 1, 11 and 12. The needle tubes 1 and the pipetting needle 4 are made of a metal material such as stainless steel or the like.

The upper and lower needle seats 2 and 3 are made from one polymer material or more polymer materials, including plastic, resin and rubber. The upper and lower needle seats 2 and 3 can be made from the same polymer material or different polymer materials. For example, the upper needle seat 2 can be made from medical polymer materials, such as epoxy resin or polypropylene, or resin/plastic composite materials, such as epoxy resin/polypropylene, the lower needle seat 3 can be made from materials such as polypropylene, polyvinyl chloride, polyethylene or the like, the structural adhesive 6 can be selected from medical adhesive materials such as epoxy resin, and they can be manufactured by existing and ripening processing techniques. As a preferred embodiment, the upper or lower needle seat can be made from one polymer material, and tight fit is established by direct contact between the needle tube and the upper needle seat and/or between the pipetting needle and the lower needle seat, without needing any other materials and associated fixing and sealing structures, as shown in FIG. 11.

Figure 2:
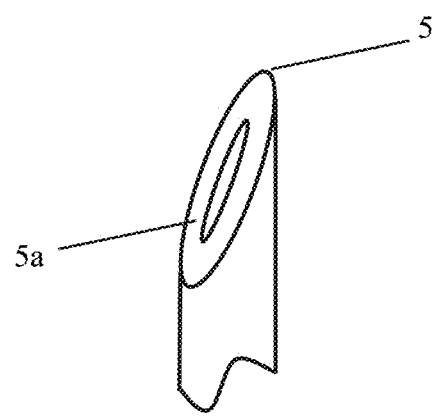
FIG. 2 is a schematic view of a structure of a needle tip for a miniature metal needle tube in the first embodiment of the invention.
Figure 3:
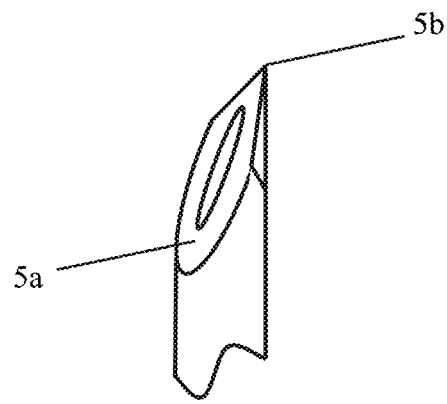
FIG. 3 is a schematic view of a structure of a needle tip for a further miniature metal needle tube in the first embodiment of the invention.

FIG. 2 is a schematic view of a structure of a needle tip for the miniature metal needle tube and the pipetting needle according to this embodiment. The needle tip 5 for the needle tube 1 and the pipetting needle 4 has an end comprising an elliptical torus 5a, wherein the elliptical torus 5a forms an angle of 5 degrees to 88 degrees with regard to an axial direction of the needle tube 1. Preferably, for the purpose of further improving painless, safe and convenient injection of the injection with the injection needle head of the embodiment, at least a segment of an arc surface is cut away from the elliptical torus 5a to form a sharp angle 5b shown in FIG. 3. The needle tip can be provided at one end or two opposite ends of the needle tube 1 and the pipetting needle 4. A case wherein two needle tips are provided at two opposite ends of the pipetting needle 4 is more applicable to the condition where the inner diameter of the fixing groove 16 is smaller than or equal to the inner diameter of the through-hole 23 or the outer diameter of the pipetting needle 4, and as a result, the pipetting needle can be inserted into the fixing groove much easier. The injection being transferred from the injection reservoir into the cavity 15 can also be ensured, even if the pipetting needle extending through the cavity 15 abuts against a bottom of the upper needle seat 2, as shown in FIG. 12. The miniature metal needle tube 1 has an outer diameter of 80 μm to 400 μm and an inner diameter of 30 μm to 200 μm. There is a height of 0.2 mm to 5 mm from a top end of the upper needle seat 2 to the needle tip 5. The needle tubes 1 with these dimensions are thin, short and solid and can perform vertical hypodermic (subcutaneous) injection of the injection rapidly at sites such as abdomen, arms, thighs, buttock etc, without needing to pinch skin, while a potential trouble that the injection be injected directly into muscles can be totally avoided. The pipetting needle 4 has an outer diameter of 120 μm to 1000 μm and an inner diameter of 50 μm to 500 μm. There is a length of 0.2 mm to 15 mm from a bottom end of the fixing grove to the needle tip.

Example 2

Figure 4:
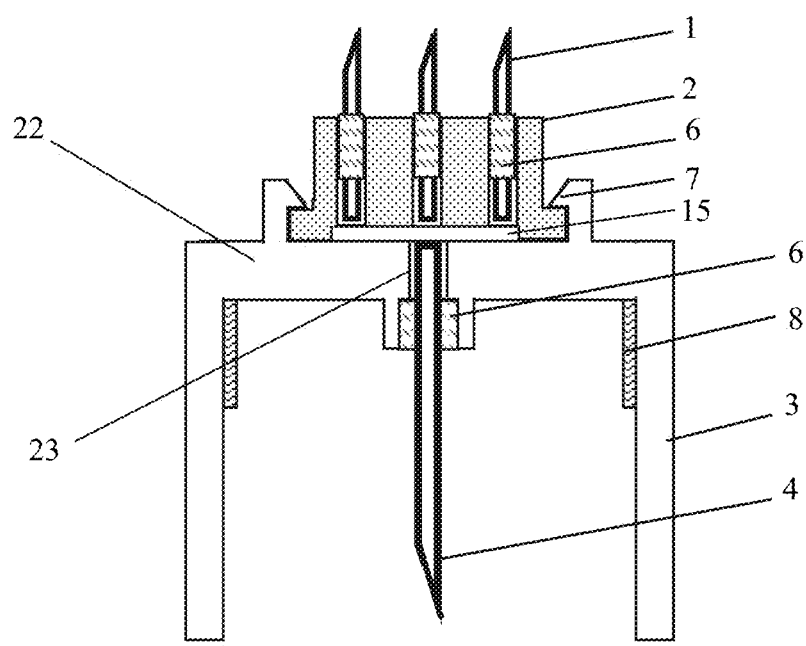
FIG. 4 is a cross sectional view of a structure of a disposable array-type micro injection needle head according to a second embodiment of the invention, in which an upper needle seat is provided with an integral outlet array.

FIG. 4 is a cross sectional view of a structure of an injection needle head according to an embodiment in which an upper needle seat is provided with an integral outlet array. The injection needle head in this embodiment is structurally similar to that in the first embodiment, with a main difference in that the upper needle seat 2 is a curved substrate, integrally formed with which is an array called as a positioning notch array or outlet array 12, i.e., at least two positioning notches or outlets 12 are provided in the upper needle seat 2. The number and the arrangement of the positioning notches or outlets 12 are determined according to the number and the desired arrangement of the needle tubes 1, and the needle tubes 1 are fixed in the positioning notches or outlets 12 with structural adhesive 6.

Figure 5:
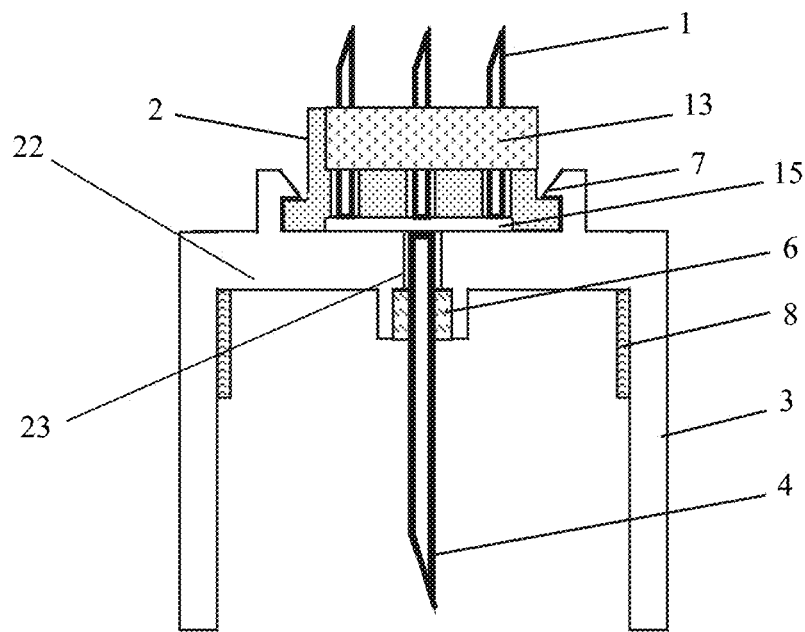
FIG. 5 is a cross sectional view of a structure of a further disposable array-type micro injection needle head according to the second embodiment of the invention, in which an upper needle seat is provided with an integral outlet array and is provided with a recess in its side wall.

FIG. 5 is a cross sectional view of a structure of an injection needle head according to an embodiment of the invention, in which an upper needle seat is provided with an integral outlet array and is provided with a recess in its side wall. The injection needle head in this embodiment is structurally similar to the injection needle head shown in FIG. 4, with a main difference in that the recess 13 is provided in the side wall of the upper needle seat 2. Structural adhesive is filled in the recess 13 and surrounds the miniature metal needle tubes 1, and the miniature metal needle tubes 1 are fixed in the positioning notches or outlets 12 of the upper needle seat 2 with the structural adhesive.

Figure 6:
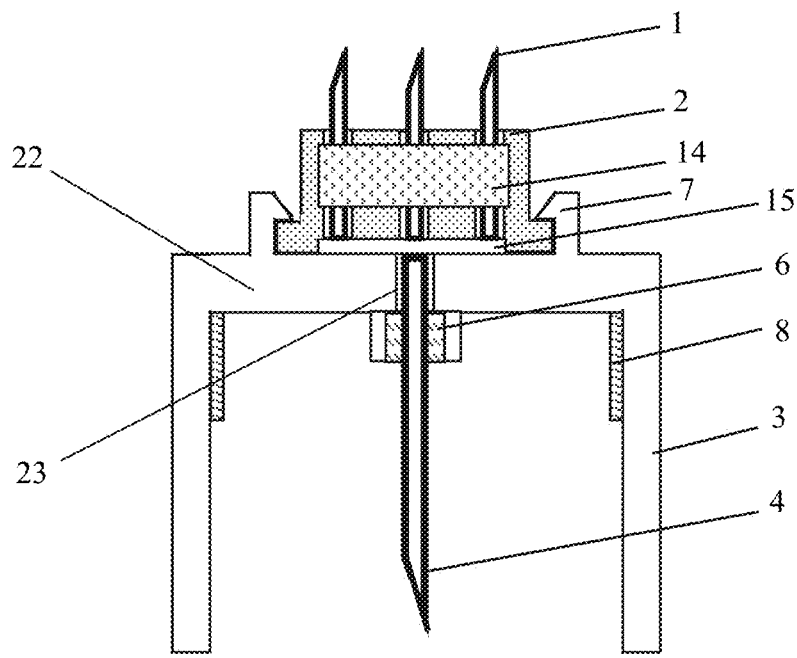
FIG. 6 is a cross sectional view of a structure of a still further disposable array-type micro injection needle head according to the second embodiment of the invention, in which an upper needle seat is provided with an integral outlet array and is provided with an opening in its side wall.

FIG. 6 is a cross sectional view of a structure of an injection needle head according to an embodiment of the invention, in which an upper needle seat is provided with an integral outlet array and is provided with an opening in its side wall. The injection needle head in this embodiment is structurally similar to the injection needle head shown in FIG. 5, with a main difference in that the opening 14 is provided in the side wall of the upper needle seat 2. Structural adhesive is filled in the opening 14 and surrounds the miniature metal needle tubes 1, and the miniature metal needle tubes 1 are fixed in the positioning notches or outlets 12 of the upper needle seat 2 with the structural adhesive.

Figure 7:
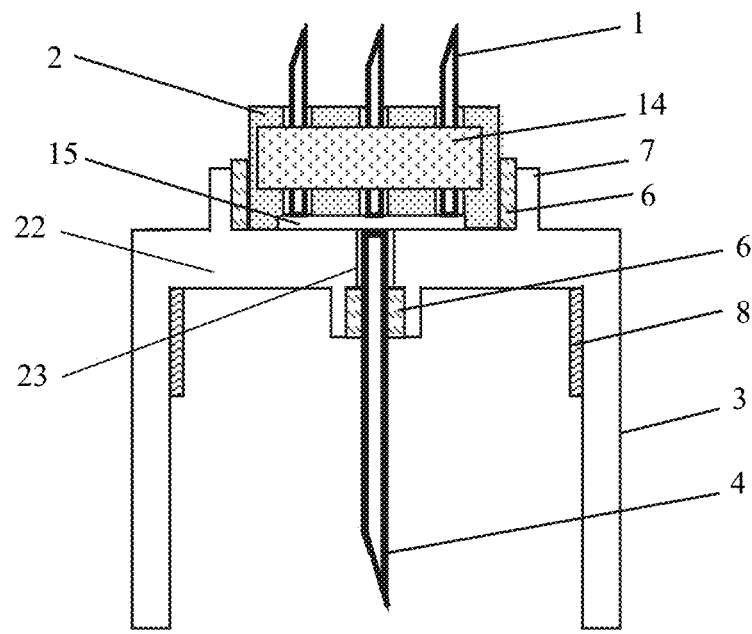
FIG. 7 is a cross sectional view of a structure of another disposable array-type micro injection needle head according to the second embodiment of the invention, in which an upper needle seat is provided with an integral outlet array and is provided with an opening in its side wall.

FIG. 7 is a cross sectional view of a structure of an alternative injection needle head according to the embodiment, in which an upper needle seat is provided with an integral outlet array and is provided with an opening in its side wall. This injection needle head is structurally similar to the injection needle head shown in FIG. 6, with a main difference in that a positioning wall of a lower needle seat is not provided with a projecting snap portion at an end opening, and fixing and sealing between the upper and lower needle seats are achieved only by means of structural adhesive.

Figure 8:
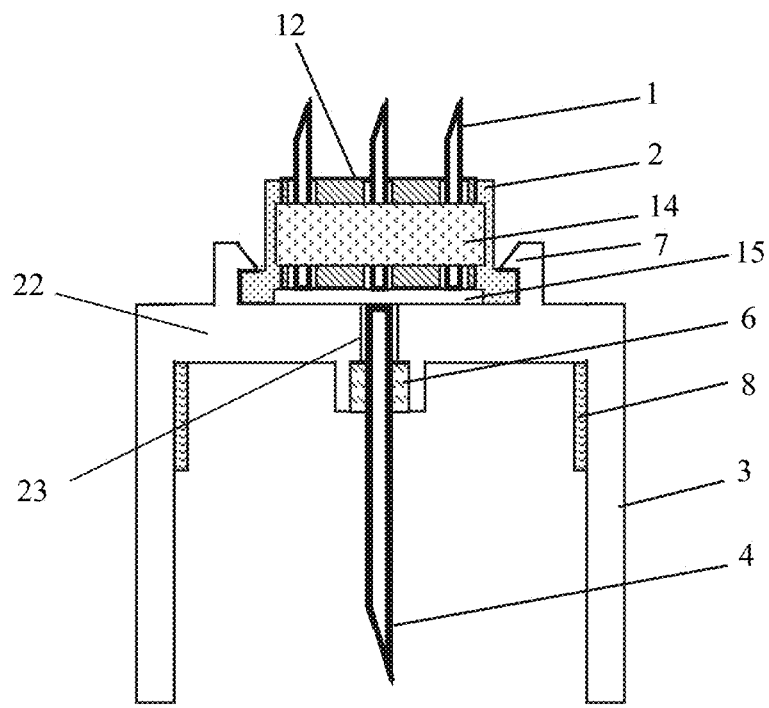
FIG. 8 is a cross sectional view of a structure of a further injection needle head according to the second embodiment of the invention, in which an upper needle seat is provided with an outlet array and provided with an opening in a side wall, the outlet array being separated formed from the upper needle seat.

FIG. 8 is a cross sectional view of a structure of an injection needle head according to an embodiment, in which an upper needle seat is provided with an outlet array and provided with an opening in a side wall, the outlet array being separated formed from the upper needle seat. This injection needle head is structurally similar to the injection needle head shown in FIG. 6 with a main difference in that the upper needle seat is separately formed from positioning notches or outlets 12. Structural adhesive is filled in the opening 14 and surrounds the miniature metal needle tubes 1, and structural adhesive functions to fix the miniature metal needle tubes 1 in the positioning notches or outlets 12 of the upper needle seat 2 and to adhesively fix between the upper needle seat and the positioning notches or outlets 12, assembling the upper needle seat and the positioning notches or outlets 12 into one piece.

In this embodiment, both the upper needle seat 2 and a lower needle seat 3 are made from materials such as polypropylene, polyvinyl chloride, polyethylene or the like, the structural adhesive can be selected from medical structural adhesive, for example epoxy resin, and they can be manufactured by existing and ripening processing techniques.

Figure 9:
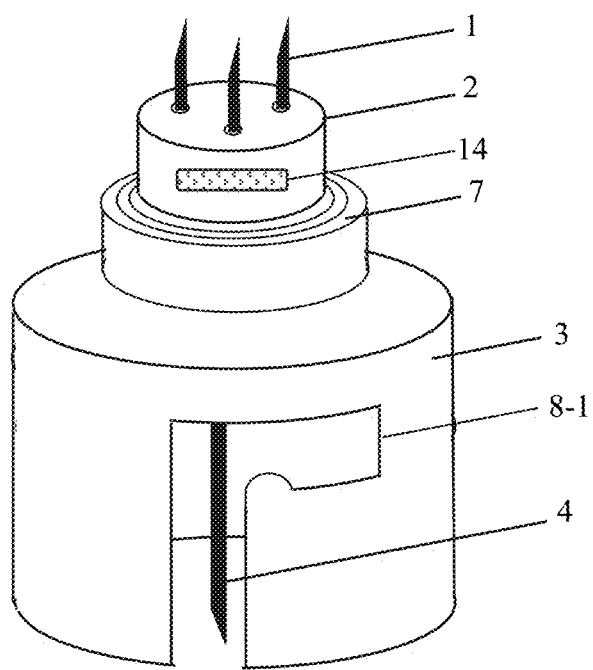
FIG. 9 is a cross sectional view of a structure of a further injection needle head according to the second embodiment of the invention, in which a lower needle seat is provided with a snap portion.
Figure 10:
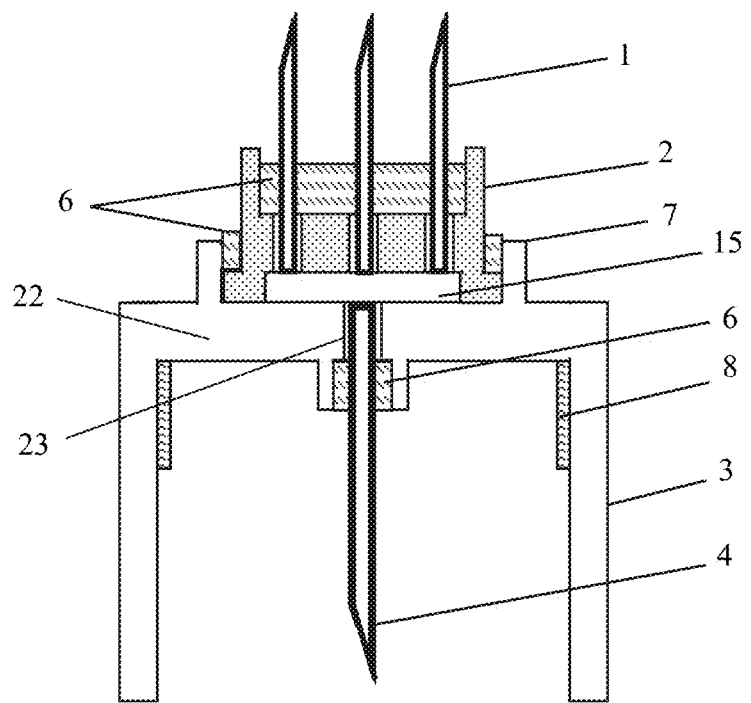
FIG. 10 is a cross sectional view of a structure of a disposable array-type micro injection needle head according to the first embodiment of the invention, in which structural adhesive is used for fixing and sealing.

FIG. 9 is a cross sectional view of a structure of an injection needle head according to an embodiment, in which a lower needle seat is provided with a snap portion. This injection needle head is structurally similar to any one of the injection needle heads shown in FIGS. 1 and 4 to 8 with a main difference in that the lower needle seat 3 is provided with a fixing snap portion 8-1 in a side wall of a cylindrical column which is similar to that in the first embodiment. Specially choosing the fixing snap portion or a threaded portion depends on the detail interface structure of an injection reservoir, and other corresponding interface structures can also be used.

Example 3

Figure 14:
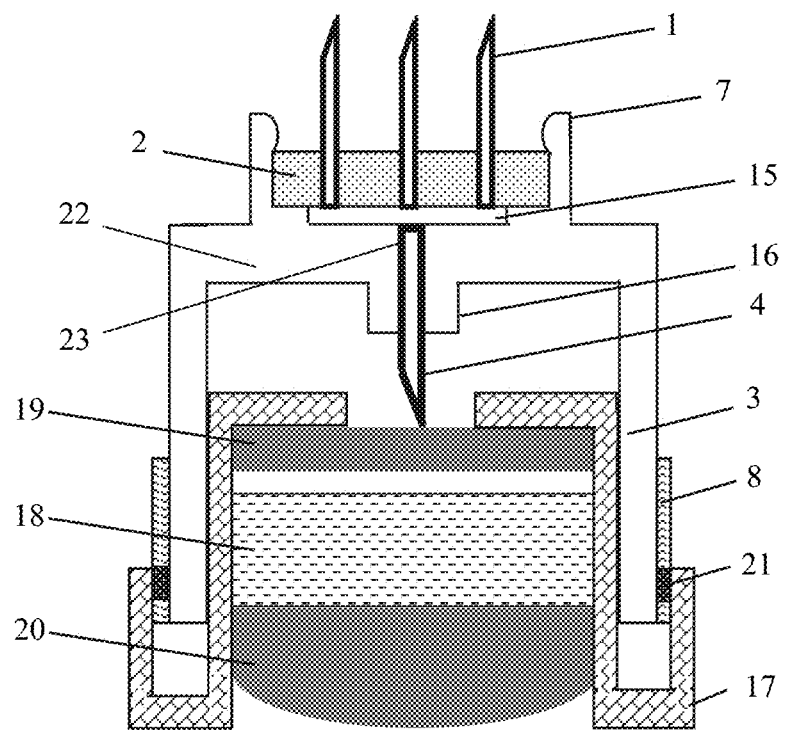
FIG. 14 is a cross sectional view of a structure of a disposable prefilled syringe according to a third embodiment of the invention.

FIG. 14 is a cross sectional view of a structure of a disposable prefilled syringe incorporating the disposable array-type micro injection needle head described above according to an embodiment of the invention, in which the disposable prefilled syringe comprises the disposable array-type micro injection needle head and an injection reservoir with capacity scales, and in which the injection reservoir is connected to the disposable array-type micro injection needle head by screw threads and/or a fixing snap portion, allowing relative movement between the two. The injection reservoir is an enclosed container 17 prefilled with medicine liquid 18 and is located or partially located in the cylindrical column of the lower needle seat 3. The enclosed container 17 has a top end 19 easy to be punctured by the pipetting needle and a bottom end at which a movable component or piston 20 is provided, the movable component or piston 20 being configured for sealing injection in the enclosed container 17. In use, the enclosed container 17 is manually rotated and/or pressed to be moved toward the disposable array-type micro injection needle head. Then, the pipetting needle 4 punctures into the top end of the enclosed container 17 and the movable component or piston 20 at the bottom end of the enclosed container 17 is pushed to press the injection through the pipetting needle to be injected out. The disposable array-type micro injection needle head and the injection reservoir are assembled into one piece, and then the assembly is sterilized and enclosed within the needle seat protecting sleeve. Otherwise, the disposable array-type micro injection needle head and the injection reservoir are stored separately from each other when not in use and are assembled into one piece when desired.

Various products in the embodiments described as above can be produced by existing and ripening processing techniques and from conventional or novel medical materials. The disclosure described herein is only part of preferred embodiments of the invention. The products described herein can not only be used with an existing insulin pen in combination, but also can be used with any existing or future syringes for other medicine in combination in case of incorporating appropriate interface structures into the products.

The disclosure described above is merely preferred embodiments of the invention. It should be noted that various developments and substitutions made by a skilled in the art without departure from the technical principle of the invention should be considered as falling within the protecting scope of the invention.

What is claimed is:

1. A disposable array-type micro injection needle head, characterized by comprising: a lower needle seat which is configured as a cylindrical column opening at one end and having a top cap at the other end and which is configured to be connected with an injection reservoir; an upper needle seat which is located above the top cap of the lower needle seat with a cavity formed between the upper needle seat and the top cap; a through-hole formed in the top cap which is configured for communicating the cylindrical column with the cavity, wherein a pipetting needle is mounted in the through-hole which has one end communicated with the cavity and the other end located in the cylindrical column and which is configured for extracting injection from the injection reservoir into the cavity; and at least two needle tubes mounted in the upper needle seat, each of which has one end comprising a needle tip for puncturing and for injecting the injection and the other end for mounting on the upper needle seat and for communicating with the cavity, wherein the upper needle seat is a flat substrate or a curved substrate, the upper needle seat is provided with positioning notches or outlets which have a corresponding number with the needle tubes, and the needle tubes are fixed in corresponding positioning notches or outlets by means of the structure of the positioning notches or outlets themselves or with structural adhesive, wherein each of the lower needle seat and the upper needle seat differentiating from each other is an individually formed member, a positioning wall is provided above the top cap, the positioning wall is integrally formed with the lower needle seat and configured for fixing and sealing the upper and lower needle seats, wherein a fixing groove, which is coaxial and in communication with the through-hole, is provided under the top cap, wherein the fixing groove has an inner diameter equal to or larger than an inner diameter of the through-hole or an outer diameter of the pipetting needle, and the pipetting needle extending through the fixing groove is sealingly fixed in the fixing groove and in the through-hole by means of the structure of the fixing groove itself or structural adhesive.

2. The disposable array-type micro injection needle head according to claim 1, characterized in that the upper needle seat is fixed and sealed to the positioning wall by means of structural adhesive or rubber pads or combination thereof.

3. The disposable array-type micro injection needle head according to claim 1, characterized in that the lower needle seat is provided on an inner wall or outer wall of the cylindrical column with screw threads and/or fixing snap-slots, so that the lower needle seat is detachably connected with the injection reservoir.

4. The disposable array-type micro injection needle head according to claim 1, characterized in that the needle tube has an outer diameter of 80 μm to 400 μm and an inner diameter of 30 μm to 200 μm, and there is a height of 0.2 mm to 5 mm from a top end of the upper needle seat to the needle tip, and in that the pipetting needle has an outer diameter of 120 μm to 1000 μm and an inner diameter of 50 μm to 500 μm, and there is a length of 0.2 mm to 15 mm from a bottom end of the fixing groove to the needle tip.

5. The disposable array-type micro injection needle head according to claim 1, characterized in that the needle tip is provided at one end or at two opposite ends of the needle tube and of the pipetting needle, wherein the needle tip comprises an elliptical torus or has at least a segment of an arc surface cut from the elliptical torus to form a sharp angle, the elliptical torus forming an angle of 5 degrees to 88 degrees with regard to an axial direction of the needle tube.

6. The disposable array-type micro injection needle head according to claim 1, characterized in that the positioning notches or outlets are integrally or separately formed with the upper needle seat.

7. The disposable array-type micro injection needle head according to claim 1, characterized in that the upper needle seat is provided with at least one opening or recess in its side wall, and structural adhesive is filled in the opening or recess and surrounds the needle tubes to fix them in the positioning notches or outlets of the upper needle seat.

8. The disposable array-type micro injection needle head according to claim 1, characterized by a needle tube protecting sleeve provided over the upper needle seat, a needle seat protecting sleeve provided over the upper and lower needle seats, and a sealing material layer provided at an opening at a lower portion of the needle seat protecting sleeve, wherein the sealing material layer is preferably a sealing paper.

9. The disposable array-type micro injection needle head according to claim 1, characterized in that the needle tube and the pipetting needle are made of a metal material, and the upper and lower needle seats are made from one polymer material or more polymer materials, the polymer including plastic, resin and rubber.

10. The disposable array-type micro injection needle head according to claim 9, characterized in that the upper needle seat and/or the lower needle seat is made from one polymer material, and a tight fit is established by direct contact between the needle tube and the upper needle seat and/or between the pipetting needle and the lower needle seat.

11. A disposable prefilled syringe comprising: an disposable array-type micro injection needle head comprising: a lower needle seat which is configured as a cylindrical column opening at one end and having a top cap at the other end and which is configured to be connected with an injection reservoir; an upper needle seat which is located above the top cap of the lower needle seat with a cavity formed between the upper needle seat and the top cap; a through-hole formed in the top cap which is configured for communicating the cylindrical column with the cavity, wherein a pipetting needle is mounted in the through-hole which has one end communicated with the cavity and the other end located in the cylindrical column and which is configured for extracting injection from the injection reservoir into the cavity; and at least two needle tubes mounted in the upper needle seat, each of which has one end comprising a needle tip for puncturing and for injecting the injection and the other end for mounting on the upper needle seat and for communicating with the cavity, wherein the upper needle seat is a flat substrate or a curved substrate, the upper needle seat is provided with positioning notches or outlets which have a corresponding number with the needle tubes, and the needle tubes are fixed in corresponding positioning notches or outlets by means of the structure of the positioning notches or outlets themselves or with structural adhesive, wherein each of the lower needle seat and the upper needle seat differentiating from each other is an individually formed member, a positioning wall is provided above the top cap, the positioning wall is integrally formed with the lower needle seat and configured for fixing and sealing the upper and lower needle seats; wherein a fixing groove which is coaxial and in communication with the through-hole, is provided under the top cap, wherein the fixing groove has an inner diameter equal to or larger than an inner diameter of the through-hole or an outer diameter of the pipetting needle, and the pipetting needle extending through the fixing groove is sealingly fixed in the fixing groove and in the through-hole by means of the structure of the fixing groove itself or structural adhesive; and the injection reservoir, wherein the injection reservoir is an enclosed container prefilled with medicine liquid and is located or partially located in the cylindrical column of the lower needle seat, wherein the container has a top end able to be punctured by the pipetting needle and a bottom end at which a movable component or piston is provided, and wherein, in use, the container is manually rotated and/or pressed so that the pipetting needle punctures into the top end of the container and the movable component or piston at the bottom end of the enclosed container presses injection through the pipetting needle to be injected out.

12. The disposable prefilled syringe according to claim 11, characterized in that the disposable array-type micro injection needle head and the injection reservoir are assembled into one piece, and the assembly is sterilized and enclosed within the needle seat protecting sleeve, or in that, the disposable array-type micro injection needle head and the injection reservoir are stored separately from each other when not in use and are assembled into one piece when desired.

13. The disposable prefilled syringe according to claim 11, characterized in that a positioning wall, which is integrally formed with the lower needle seat and which is configured for fixing and sealing the upper and lower needle seats, is provided above the top cap.

14. The disposable prefilled syringe according to claim 13, characterized in that the upper needle seat is fixed and sealed to the positioning wall by means of structural adhesive or rubber pads or combination thereof.

* * * * *